United States Patent [19]

MacLean et al.

[11] Patent Number: 5,675,251
[45] Date of Patent: Oct. 7, 1997

[54] DEVICE AND METHOD FOR INSPECTION OF PIPELINES

[75] Inventors: M. Douglas MacLean, Ardrossan; Paul P. Pastushak; Gordon R. Brandly, both of Edmonton, all of Canada

[73] Assignee: Hydroscope Inc., Edmonton, Canada

[21] Appl. No.: 271,713

[22] Filed: Jul. 7, 1994

[51] Int. Cl.⁶ .......................... G01N 27/72; G01N 33/12
[52] U.S. Cl. ........................................................ 324/220
[58] Field of Search .................... 324/219–221, 324/226; 73/623, 638

[56] References Cited

U.S. PATENT DOCUMENTS

| | | |
|---|---|---|
| 2,573,799 | 11/1951 | Maclean . |
| 2,992,390 | 7/1961 | De Witte . |
| 3,060,377 | 10/1962 | Schmidt . |
| 3,243,697 | 3/1966 | Schmidt . |
| 3,417,325 | 12/1968 | McCullough . |
| 3,532,969 | 10/1970 | McCullogh . |
| 4,292,588 | 9/1981 | Smith . |
| 4,292,589 | 9/1981 | Bonner . |
| 4,372,161 | 2/1983 | de Buda et al. ............... 73/432 |
| 4,546,314 | 10/1985 | Minerbo . |
| 4,621,532 | 11/1986 | Takagi et al. ............... 324/220 |
| 4,633,177 | 12/1986 | David et al. ............... 324/220 |
| 4,770,105 | 9/1988 | Takagi et al. ............... 104/138.2 |
| 4,808,924 | 2/1989 | Cecco . |
| 4,808,927 | 2/1989 | Cecco . |
| 4,855,676 | 8/1989 | Cecco . |
| 4,866,978 | 9/1989 | Biggerstaff ............... 73/405 |
| 5,049,817 | 9/1991 | Cecco . |
| 5,204,622 | 4/1993 | McCaslin et al. ............... 324/220 |
| 5,214,379 | 5/1993 | Chern ............... 324/220 |
| 5,313,838 | 5/1994 | Gondard et al. ............... 73/623 |
| 5,329,824 | 7/1994 | Carapezza et al. ............... 73/623 |
| 5,365,331 | 11/1994 | Tamburrino et al. ............... 356/241 |
| 5,398,560 | 3/1995 | Zollingger et al. ............... 73/865.8 |
| 5,402,065 | 3/1995 | Tabari et al. ............... 324/220 |
| 5,453,688 | 9/1995 | Cecco et al. ............... 324/220 |
| 5,454,276 | 10/1995 | Wernicke ............... 73/865.8 |
| 5,532,587 | 7/1996 | Downs et al. ............... 324/220 |

FOREIGN PATENT DOCUMENTS 0065325  11/1982  European Pat. Off. .

OTHER PUBLICATIONS

Non–Destructive Testing of Water Mains for Physical Integrity AWNA Research Foundation and American Water Works Assoc. 1992.

History of Remote–Field Eddy Current Inspection Technique T.R. Schmidt 1989.

*Primary Examiner*—Walter E. Snow
*Attorney, Agent, or Firm*—Bennett Jones Verchere

[57] ABSTRACT

A device is taught for inspecting the integrity of water distribution pipelines. The device is constructed of housing units, for housing inspection circuitry, which are generally spherical in shape. The housing units are connected by flexible connectors which can, in some embodiments, allow for communication between the units. As such, the device is able to negotiate bends and pass through openings of reduced size in the pipeline. The device can be used with various inspection technologies including remote field eddy current inspection technology. A method for inspecting the integrity of a water pipeline system is disclosed wherein water hydrants can be used to access the system.

30 Claims, 2 Drawing Sheets

DEVICE AND METHOD FOR INSPECTION OF PIPELINES

FIELD OF THE INVENTION

The present invention relates to a method and device for inspection of pipelines and, in particular, the present invention relates to a method and device for inspection of the physical integrity of water distribution pipelines.

BACKGROUND OF THE INVENTION

Many water distribution systems throughout the world have been in use for periods approaching or exceeding a century. Over time, the water systems have received varying degrees of maintenance, however, inspection is difficult without costly excavation. Often, no action is taken until a leak is detected, at which time the section surrounding the leak is excavated and repaired. System maintenance has often been limited to monitoring the failure rates for individual lines and performing replacement of an entire line or a long segment of it when leak frequency has exceeded tolerable values. This approach may lead to unnecessary replacement of considerable good pipe. As a result, there exists a need for a cost effective method to ascertain line condition. Since water lines are almost always buried, any applicable inspection method must be capable of operating solely within the bore of the pipe, to detect flaws such as corrosion and cracks through the entire thickness of the pipe.

In order to make inspection cost effective, it must be possible to perform the inspection with minimal preparation of the line, and, in particular, without having to excavate the lines. This means that the inspection device must be capable of accessing the line through existing access points, such as hydrants. The water pressure in lines is generally about 80 PSIG, and can reach pressures of 120 PSIG. The inspection device must be able to withstand such water pressures.

The inspection method must be of useable with pipes made of inhomogeneous materials, such as cast iron. In addition, the presence of right-angle elbows and tees, large numbers of service taps and fittings, and the relatively large accumulations of scale typical of municipal water systems requires the use of a device which is flexible and able to flex around bends and fit through small openings.

There are several methods of inspection which offer the possibility of measuring pipe condition from the inside, and which are used for this purpose in other applications. Among these are ultrasonic, magnetic flux leakage, eddy current, and remote field eddy current technology.

Ultrasonic methods are used extensively to measure the thickness of many materials with one sided access only, and exhibit very good accuracy in most steels. Unfortunately, they do not work well in cast iron, because the grain size in cast iron approaches the ultrasonic wave length. This results in severe scattering and attenuation of the acoustic signal.

Flux leakage methods are used extensively in oil well casing and petroleum pipeline applications. They are limited by the requirements that the pipe be very clean inside to prevent sensor bounce, and that a substantially constant speed be maintained. The scale build-up typical of water lines prevents flux leakage inspection, as does the relatively great wall thickness of these lines. In addition, while this method is effective for the detection of localized sharp edged pits and cracks, it is very insensitive to general overall wall loss.

Eddy current methods have been the technique of choice for many years in the inspection of non-magnetic metal piping in applications such as air conditioning units and non-ferrous chemical process piping. In magnetic materials such as cast irons and carbon steels, the depth of penetration of eddy currents is greatly reduced, precluding inspection of the outside of the pipe, particularly when the pipe is of appreciable thickness. Attempts have been made to overcome this limitation by the use of constant magnetic fields to reduce the effective magnetic permeability of the material, but the thickness of typical water lines and the presence of scale make this method impractical for the inspection of these lines. Also, eddy current probes react strongly to changes in the distance between the sensors and the material under inspection, which requires that the inside of the pipe be very clean. For these reasons, this is not a viable method for water line applications.

Remote field eddy current (RFEC) is a relatively new electromagnetic inspection method which has become prominent in the last few years. The term "remote field eddy current" is used to describe the technique in which an alternating magnetic field is induced in the pipe by an excitation or source coil and the field as modified by the pipe material is detected at a location remote from the exciter coil. The detector must be spaced from the exciter coil a sufficient distance to eliminate direct coupling within the pipe between the exciter coil and the detector, and thereby overcome the problems associated with traditional eddy current methods. From classic eddy current equations one can derive an equation illustrating that flux density at any depth will be attenuated and delayed in time (shifted in phase) in a manner related to metal thickness. In particular, eddy current instruments detect a flaw by measuring the reduced attenuation, time delay and field direction the flaw produces as compared with a normal wall thickness. This perturbation in the inner wall electromagnetic field pattern caused by a flaw is highly localized in the vicinity of the flaw and will, to a limited extent, outline the shape of the flaw.

SUMMARY OF THE INVENTION

The present invention provides a method and apparatus for inspection of water distribution pipelines by various methods including remote field eddy current. Using RFEC the physical integrity on both the inside and outside of the pipes can be ascertained without requiring access to the exterior of the pipe.

According to a broad aspect of the present invention, there is provided an inspection device for pipelines comprising a series of housing units having a shape suitable for moving through a pipeline system, and a flexible connector extending between each of the housing units in series.

An embodiment of the device according to the present invention incorporates remote field eddy current inspection technology.

According to a further broad aspect of the present invention there is provided a process for inspecting a water distribution pipeline system using the inspection device of the present invention comprising:

feeding the inspection device into the system through an access point;

moving the device through the system; and removing the device from the system.

According to a still further broad aspect of the present invention there is provided a process for inspecting interior and exterior surfaces and wall thickness of a water distribution pipeline system comprising:

feeding an inspection device into the system through an above-ground access point;

moving the device through the system; and
removing the device from the system,

DESCRIPTION OF THE INVENTION

A device is provided for inspecting the integrity of water distribution pipelines by moving along the inner bore of the pipelines of the system. The device can be used with RFEC, and various other inspection technologies. The device is able to negotiate the hydrants, tees, elbows and valves encountered in such a pipeline due to its "balls-on-a-string" design. The "balls" are a plurality of housing units in series, while the string is a flexible connector which extends between each consecutive housing unit.

The housing units house the internal circuitry of the device. As such, the housing units are sealed to prevent the entry of water into the unit. Preferably, the units are formed of high strength, waterproof, pressure resistant and abrasion resistant materials such as, for example, the thermoplastics Delrin™ and Nylatron™, stainless steel or similar materials. The units are sealed by means of O-rings and the like or, alternatively, by use of tapered thread fittings. To facilitate the movement of the housings along the pipeline, each housing unit is of a size suitable for passing through the pipeline bore. As an example, a housing having a diameter of 4" is preferred for use in the 6" (internal diameter) pipe commonly used in water distribution lines. In addition, the housing units are shaped to be stream-lined. Preferably, the leading end of the housing units are generally rounded such that they will not catch on joints, corners or discontinuities along the pipe bore. Preferably, both the leading end and the trailing end of each housing unit will be rounded to facilitate the entry of the device into the pipe as well as the removal of the device along the same path. Preferably, the housing units are substantially spherical or ovoid.

To facilitate the negotiation of tees and elbows in the pipeline, the housing units should be compact and, thus, will carry a limited amount of circuitry in each unit. In the preferred embodiment, circuitry is positioned within the units in engagement with a central shaft by means of mechanical spacers and screws which provides for easy assembly. The number of units used, then, will relate to the amount of circuitry incorporated in the device and the space requirements of the circuitry. Any number of units can be strung together to form the device.

To facilitate the negotiation of bends in the pipeline by the device, the units are mounted on a flexible connector, such as wire or rope. Where communication is required between the units, such as for electrical connection, a flexible tubular element can be used. The flexible tubular element is attached between the housing units to maintain the seal against water. Preferably, the tubular element is a stainless steel jacketed, Teflon™ lined hydraulic-type hose with threaded pressure connectors for attachment to the housing units. The seal is maintained at the connection by use of a tapered thread design along with the use of Teflon™ tape or the like. The length of the connector between each unit is sufficient to allow the device to flex around bends which is generally equivalent to about 0.8 to 3.5 pipe bore diameters.

The device can be fitted with means for connection to lines at the leading and trailing end of the device. The connection can be simply to a pulling line for moving the device along the pipe by any suitable motive means, such as an above-surface pulling means or pig. The attached lines can provide for distance determination to accurately determine the tool position along the pipe. In addition, the connection may include a sealed flexible connector as is used between housings to allow communication to the surface, such as for power sources or data transmission. Alternatively, a wireline having an outer armour can be used for transmission and power supply.

In use, the device is fed into a pipeline system through an access point. Preferably, the access point is a hydrant, thereby avoiding excavation to locate an access point. Where a pulling line is used with the device, the pulling line is fed into the hydrant and pulled through the pipeline by means of a pig which is driven by water or air pressure.

The device moves along the pipeline by the desired motive means and inspects the pipeline using the desired technology. The data collected can be stored internally of the housing units or transmitted to the surface for real time analysis.

Pipelines of any length can be inspected, however lengths of up to 1000 m can be reasonably inspected because of limitations in trailing or pulling cables. The pipeline is preferably first cleaned of rust and debris by use of a scraper pig or brush. This facilitates inspection and movement of the device along the pipeline.

The section of pipe to be inspected can be sealed off or alternatively, can contain flowing fluid.

Where the device uses RFEC for inspection, the leading unit will be attached to a line for movement along the pipe by use of a pig or surface pulling means. This unit is attached by flexible connector to the next consecutive housing unit. This leading unit can be an empty unit, since it will be the first unit to encounter snags or blockages, or it can house the exciter coil or other circuitry. The exciter coil generates the requisite time-varying magnetic field for use in RFEC inspection. Possible exciter coil arrangements can comprise, for example, a single circumferential coil or radially aligned multiple coils. Many combinations of wire gauge, number of turns and size are possible. In the preferred embodiment, there is provided a single circumferential exciter coil consisting of 285 turns of #25 wire, with coil length and depth being equal and resistance being 9.2 ohms. The exciter is driven by a power source such as a source of alternating current at the surface which is connected to the device through a wireline. Alternatively, the exciter coil is driven by a battery and oscillating circuitry means contained within the unit, or by such other power sources as is known in the art.

The unit housing the exciter coil, which will be referred to herein as the excitor unit, is fitted with centralizers which act to maintain the concentric positioning of the unit within the bore of the pipe and limit the abrasion of the unit. Centralizers can include, for example, rods, brushes or wheel-type expanding arms formed of durable, resilient material. Preferably, ⅛" diameter rods or brushes formed from Delrin are used.

The exciter unit is connected to a unit, which will be referred to herein as the detector unit, housing at least one detector coil, and related circuitry, which detects the magnetic field arriving at the detector resulting from the exciter coil. According to RFEC principles, the detector coil must be spaced from the exciter coil by a length of at least 2× the internal diameter of the pipe. The detector can be either partially or fully circumferential, or a combination of the two geometries. Suitable detector coil arrangements include, for example, one or more of single circumferential coils, radially aligned multiple coils, radially aligned differential coils, tipped coils designed to detect in both radial and axial directions, and "horse-shoe" and "pancake" coils with or without ferrite cores and cups. Alternatively, there can be solid state detectors such as hall-effect or magneto-resistive sensors. While many combinations of wire gauge, number of turns and size are possible, preferably, the detector arrangement consists of one or more circumferential or differential coils consisting of 3600 turns of #38 wire with equivalent coil length and depth, and resistance of 1366 ohms.

The detector coils are connected to circuitry, preferably located within the detector unit, for measuring the in-phase and quadrature components of the magnetic field at each detector coil, relative to the phase of the transmitter signal. The resulting measurements allow calculation of the pipe wall thickness adjacent each coil, as is known in RFEC technologies. The detector data is converted into a format suitable for transmission or storage.

In the transmitting embodiment, the detector unit is connected, by flexible connector means to a line driver unit containing line driver circuitry which conditions and amplifies the converted data for transmission through an electric wireline, or other mode of transmission, to the surface for storage or real time analysis. Where real time analysis is used, problem areas can be identified during the inspection and the inspection repeated and/or interpretive algorithms used to further characterize the defect. Interpretive algorithms for defect characterization are obtained by correlation of data resulting from test pipes having known defects. Correlation of data with distance information allows defects to be precisely located along the pipe.

Non-transmitting embodiments require at least one memory unit, in place of the line driver unit, which houses an electric memory module for storage of the data together with timing information. Correlation of timed data and distance information recorded at the surface allows defects to be precisely located along the length of the pipe. Using the non-transmitting embodiment, the stored data is analyzed after the inspection of the pipeline by interpretive algorithms. Preferably, the non-transmitting device includes three additional units including, a battery unit, a memory unit and a timer or distance encoder unit.

A trailing unit can be attached at the end of the transmitting or non-transmitting device for attachment to the wireline or trailing line. The trailing unit is empty and acts to provide attachment to the wireline or trailing to prevent damage to the penultimate unit when the unit is pulled back along the pipe.

While the housing units of the preferred embodiment have been described and separated according to their function it is to be understood that the device need only carry the circuitry necessary to directly inspect the pipe by RFEC and transmit the signal to the surface. While we have described the device as containing between 3 to 7 units, the number of units can vary depending the use of empty leading and trailing units and on the distribution of the circuitry throughout the units with the minimum number of units being one. This, however, would require the length of the unit to be at least 2× the diameter of the pipe and would prevent the device from negotiating bends in the pipe. Thus, the reasonable minimum number of units is two. In the preferred embodiment, the units are provided to effectively distribute the circuitry to ensure the size of each unit is suitable to easily move through water distribution pipelines.

BRIEF DESCRIPTION OF THE DRAWINGS

For a better understanding of the present invention, reference may be made by way of example to the following diagrammatic drawings, in which.

DESCRIPTION OF THE PREFERRED EMBODIMENT

Figure 1:
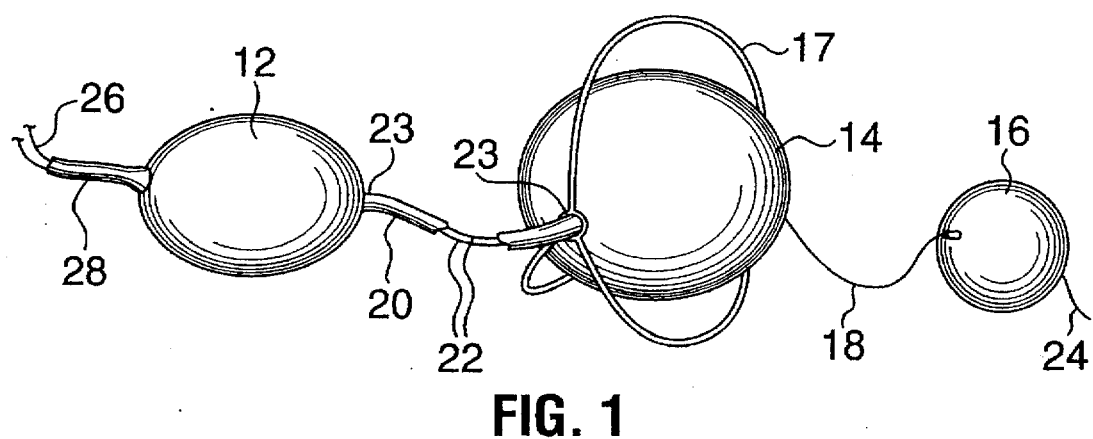
FIG. 1 is a perspective view of an inspection device of the present invention.

Referring to FIG. 1, a device 10 for inspecting the integrity of pipeline comprises a plurality of housing units 12, 14, 16 which are sized to fit within and move freely along the bore of the pipe. Each unit 12, 14, 16 is preferably substantially spherical or ovoid to prevent snagging on discontinuities within the bore. The units house inspection devices and electrical circuitry and, thus, are sealed against entry of fluids.

Where a unit of the inspection device requires axial alignment within the pipe, such as unit 14, centralizers 17 can be mounted on the unit.

The units 12, 14, 16 are connected by flexible connectors such as cable 18 or flexible tubing 20 to allow device 10 to flex around bends. Flexible tube 20 permits communication between the units and has been cut away to show use as a conduit for electrical wires 22 which extend between units 12, 14. Tube 20 is sealed at its connections 23 to units 12, 14 by tapered thread and Teflon tape to prevent entry of fluid.

Device 10 is moved along the pipeline by connection, via pulling line 24, to a pig (not shown), where fluid flow is maintained in the pipeline, or a collector such as a winch or other device (not shown).

Surface communication can be provided by wireline 26 which can be sheathed in a flexible tube 28 or its own armour.

Pulling line 24 or wireline 26 is marked to indicate the length of line to device 10 and thereby provide an indication of the device location along the pipe.

Device 10 can be used in various ways to inspect pipe condition. Preferably, the inspection is initiated through a hydrant. While other access points can be used, hydrants are preferred since excavation is avoided. The device can be used to inspect operating pipeline. Preferably, however, the section of pipeline to be inspected, including any required access hydrants, is isolated and depressurized. The device is preferably moved along the pipeline by pulling or by applied water pressure acting on a pig. After the section has been inspected, the device can be removed by pulling back along the same path or by use of an exit point such as a hydrant.

The device of the present invention allows access to pipeline via hydrants because of the flexibility of the device and compactness of the circuitry housing units.

Figure 2A:
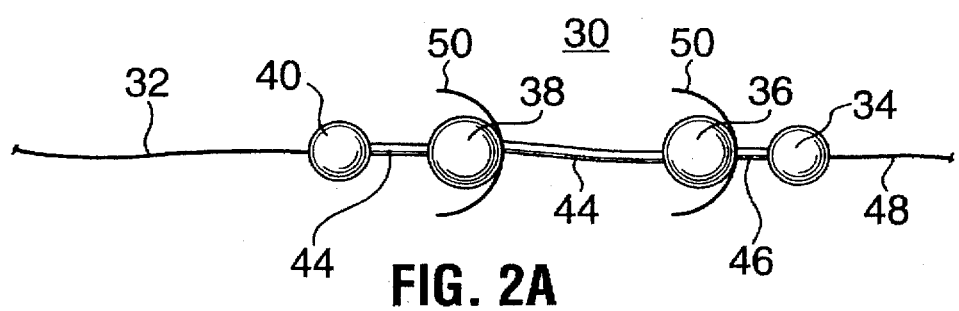
FIG. 2A is a schematic view of a transmitting embodiment of the RFEC inspection device of the present invention.
Figure 2B:
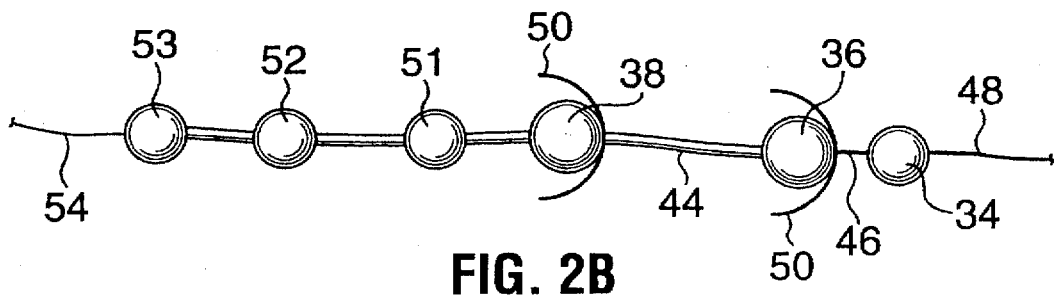
FIG. 2B is a schematic view of a non-transmitting embodiment of the RFEC inspection device of the present invention.

Referring to FIGS. 2a and 2b, an inspection device using RFEC technology may be made according to the present invention.

A first embodiment of an RFEC device 30 having electrical contact with the surface is shown in FIG. 2a. This embodiment includes an electric wireline 32 which connects to the device, either at the leading end or the trailing end, as shown. Where required, wireline 32 should be of sufficient strength to provide a means for pulling the device along the pipeline.

The wireline can provide both data transmission and power supply or, alternately, only data transmission where a power source is provided in the device. The wireline armour, such as carbon steel, is used as the ground reference. The data is transmitted along the wireline in digital form by Manchester coding and decoding. The surface data reception circuitry interfaces with a personal computer and performs functions to convert the data back into the in-phase and quadrature components of the signal seen by the detector. Presentation software displays the data on computer output. Output is in the form of four traces representing amplitude, phase, real component and imaginary component all plotted versus distance along the pipeline. Sharp changes or deflections in the traces along the pipeline are identifiable as anomalies that are considered defects on the interior or exterior surfaces of the pipe.

In the preferred embodiment, device 30 comprises five housing units including: a leading unit 34 for mechanical connection to the pulling pig or cable; an exciter unit housing an exciter coil and related circuitry 36; a detector unit housing at least one detector coil and related circuitry 38; and, a line driver unit 40 housing circuitry for conditioning and amplifying the data for transmission to the surface.

Flexible tubular connectors 44 carry electrical wires for communication between the units. Any connections which do not provide for communication between the units, such as connection 46, can be accomplished by means of cable.

The leading unit 34 is pulled by means of pulling line 48 by attachment to a pig or a surface pulling means, such as a winch (not shown).

Units 36 and 38 are maintained in axial alignment with the bore of the pipe by means of centralizers 50. Units 36 and 38 are preferably separated by a distance of 2–3× the pipe bore diameter.

An embodiment which does not transmit and, thus, does not require an electrical wireline is shown in FIG. 2b. In this embodiment, leading unit 34, exciter unit 36 and detector unit 38 remain as in the embodiment of FIG. 2a. In the preferred non-transmitting embodiment, a unit 51 is connected to detector unit 38 which houses a memory module for storing the data. Preferably, a unit 52 housing timer circuitry and a unit 53 housing the battery pack are also included in the non-transmitting device. To shorten the length of the device, the circuitry of units 51, 52 and 53 can be redistributed to remove some of these housing units.

The non-transmitting device includes a trailing line 54 to allow the device to be pulled back along the pipe. The devices of FIGS. 2a and 2b have measurement markings on their pulling lines 48, trailing line 54 or wireline 32 to permit the location of the device along the pipeline to be determined.

The device of the preferred embodiment uses analog technology to provide high resolution RFEC analysis. The circuitry design is modular, both to fit within the housing units and to alleviate problems with crosstalk, which tends to interfere with the measurement of the micro-volt level signals in the detector circuitry, and other interactions observed in earlier design approaches.

Power for the modules is provided by DC—DC converters operating from a nominal 60 VDC provided via the wireline or by batteries within the device.

Figure 3:
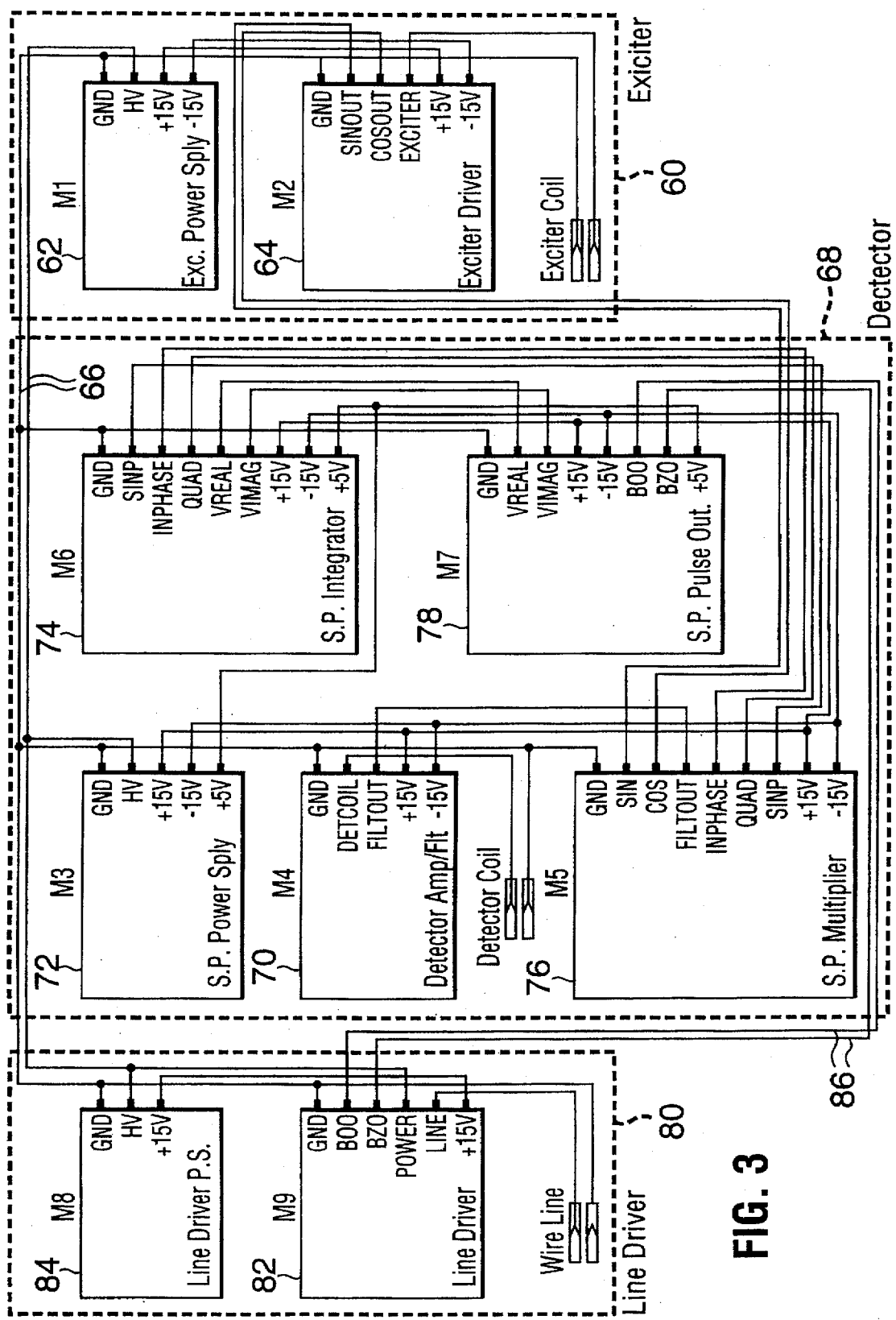
FIG. 3 is a schematic view of the circuitry of the preferred embodiment.

Referring to FIG. 3, a schematic diagram illustrates the electrical connections of the exciter unit, detector unit and line driver unit of the preferred embodiment as shown in FIG. 2A.

The exciter unit circuitry 60 comprises a exciter coil power supply 62 and a exciter coil driver 64 and provides the in-phase and quadrature signals required for the detector electronics, and the drive signal for the exciter coil. Power is supplied via lines 66 from the wireline to exciter power supply 62.

The detector unit circuitry 68 comprises a detector amplifier and filter board 70 and a signal processing system comprising a power supply 72, integrator 74, multiplier 76 and pulse output 78. Board 70 amplifies and filters the signal which is received from the detector coil.

The signal processing system converts the relative in-phase and quadrature values into proportional pulse rates.

The line driver unit circuitry 80 comprises a wireline driver 82 and power supply 84. Circuitry 80 acts to convert the pulse trains received via lines 86 from the pulse output 78 of the signal processor system into pulse trains with opposite polarity and sufficient output capability to drive the low impedance of the wireline.

The following specific example is given to further set forth the invention, it being understood that the example is by way of illustration only and is not to be construed as limiting the scope of the invention.

EXAMPLE 1

A device of the present invention and generally as described in FIGS. 2a and 3 was used to inspect a water distribution pipeline located in Northeast Calgary, Alberta, Canada. The line, measuring 200 m, was scheduled for excavation and replacement and had been in service for approximately 18 years.

The line was isolated and depressurized. The tool was then fed to the line via a standard McAvity hydrant, with the valve stem removed. Hoses from adjacent hydrants provided water pressure which acted on a pig attached ahead of the device to pull the device through the line. A wireline was attached to and trailed behind the device and provided power and data transmission to the device. The wireline was marked to provide distance information.

The device passed through the line and traversed a number of elbows and tees, as well as numerous service connections and at least one repair clamp. The device moved along the line without snagging and exited at an exit port.

Wall discontinuities along the line were located by correlating collected data with distance information gained by recording advancement of the wireline along the line.

It will be apparent that many other changes may be made to the illustrative embodiments, while falling within the scope of the invention and it is intended that all such changes by covered by the claims appended hereto.

The embodiments of the invention in which an exclusive property or privilege is claimed is defined as follows:

1. A process for inspecting a water distribution pipeline system comprising:
   providing an inspection device having a series of housing units, for housing inspection circuitry, each unit having a shape suitable for moving through a pipeline system and sealed against entry of water, a flexible connector extending between each of the housing units in series and a means for attachment to a towing means;
   feeding the inspection device into the system through a water hydrant;
   moving the device through the system; and
   removing the device from the system.

2. The process as defined in claim 1 wherein the inspection device is moved through the system by attachment to a pig.

3. The process as defined in claim 1 wherein the inspection device is moved through the system by attachment to pulling cable and surface pulling means.

4. The process as defined in claim 1 wherein the inspection device is removed by pulling back along the system and removal through the water hydrant.

5. The process as defined in claim 1 wherein the inspection device is removed through an exit hydrant.

6. A process for inspecting a water distribution pipeline system comprising:

provideing a remote field eddy current inspection device for pipelines comprising a series of housing units having a shape suitable for moving through a pipeline system, a flexible connector extending between each of the housing units in series and means for attachment to a towing means, wherein the series of housing units comprises:

a first unit sealed against entry of water and containing means for producing a time-varying magnetic field; and, a second unit sealed against entry of water and containing means for detecting a magnetic field, and the device being adapted such that the first unit and the second unit are maintained in a position during use to allow remote field eddy current inspection;

feeding the inspection device into the system through a water hydrant;

moving the device through the system; and removing the device from the system.

7. The process as defined in claim 6 wherein the inspection device is moved through the system by attachment to a pig.

8. The process as defined in claim 6 wherein the inspection device is moved through the system by attachment to pulling cable and surface pulling means.

9. The process as defined in claim 6 wherein the inspection device is removed by pulling back along the system and removal through the water hydrant.

10. The process as defined in claim 6 wherein the inspection device is removed through an exit hydrant.

11. A process for inspecting interior and exterior surfaces and wall thickness of a water distribution pipeline system comprising:

feeding an inspection device into the system through a water hydrant;

moving the device through the system; and removing the device from the system.

12. An inspection device for water pipelines comprising a series of housing units, for housing inspection circuitry, each unit being substantially spherical or ovoid in shape and sealed against entry of water, a flexible connector extending between each of the housing units in series, at least one of the flexible connectors being adapted to provide for communication between a pair of adjacent housing units and sealing means being disposed between the flexible connector and each of the pair of housing units to prevent passage of water into the housing units between which the flexible connector extends, and a means for attachment to a towing means.

13. The inspection device as defined in claim 12 wherein the flexible connectors are formed of flexible tubing.

14. The inspection device as defined in claim 12 wherein the device is sealed against entry of water at pressures of between about 80 PSIG and 120 PSIG.

15. The inspection device as defined in claim 12 wherein the device is attached to a transmitting line.

16. A remote field eddy current inspection device for pipelines comprising a series of housing units being substantially spherical or ovoid in shape for moving through a pipeline system, a flexible connector extending between each of the housing units in series, an electrical conductor extending between a pair of adjacent housing units and sealing means being disposed between the electrical conductor and each of the adjacent housing units to prevent passage of water into the housing units between which the electrical conductor extends, and means for attachment to a towing means, wherein the series of housing units comprises:

a first unit sealed against entry of water and containing means for producing a time-varying magnetic field; and, a second unit sealed against entry of water and containing means for detecting a magnetic field, and the device being adapted such that the first unit and the second unit are maintained in a position during use to allow remote field eddy current inspection.

17. The inspection device as defined in claim 16 wherein the flexible connectors are formed of flexible tubing.

18. The inspection device as defined in claim 16 wherein the series of housing units further comprises a unit sealed against entry of water and containing means for transmitting detected data along a transmitting line to a means for analyzing the data.

19. The inspection device as defined in claim 16 wherein the series of housing units further comprises a unit sealed against entry of water and containing means for storing detected data.

20. The inspection device as defined in claim 16 wherein the device is sealed against entry of water at pressures of between about 80 PSIG and 120 PSIG.

21. A remote field eddy current inspection device for water pipelines comprising a series of housing units being substantially spherical or ovoid in shape and suitable for passing through a water hydrant and a moving through a water pipeline system, a flexible connector extending between each of the housing units In series, at least one of the flexible connectors providing for communication between a pair of adjacent housing units and sealing means being disposed between the flexible connector and each of the pair of housing units to prevent passage of water into the housing units between which the flexible connector extends, and means for placing the device in tow, wherein the series or housing units comprises:

a first unit sealed against entry of water and containing means for producing a time-varying magnetic field; and, a second unit sealed against entry of water and containing means for detecting a magnetic field; and the device being adapted such that the first unit and the second unit are maintained in a position during use to allow remote field eddy current inspection.

22. An inspection device for water pipelines comprising a series of housing units for housing inspection circuitry, having a shape suitable for moving through a pipeline system and sealed against entry of water at pressures of between about 80 PSIG and 120 PSIG; a flexible connector extending between each of the housing units in series, at least one of the flexible connectors being adapted to provide for communication between a pair of adjacent housing units and sealing means being disposed between the flexible connector and each of the pair of housing units to prevent passage of water into the housing units between which the flexible connector extends, and a means for attachment to a towing means.

23. The inspection device as defined in claim 22 wherein the flexible connectors are formed of flexible tubing.

24. The inspection device as defined in claim 22 wherein the device is attached to a transmitting line.

25. The inspection device as defined in claim 24 wherein the transmitting line is adapted foe use in pulling the device and is marked to indicated distance measurements.

26. A remote field eddy current inspection device for pipelines comprising a series of housing units having a shape suitable for moving through a pipeline system, a flexible connector extending between each of the housing units and sealing means being disposed between the electrical conductor and each of the adjacent housing units to prevent passage of water at pressures of between about 80 PSIG and 120 PSIG into the housing units between which the electrical conductor extends, and means for attachment to a towing means, wherein the series of housing units comprises:

a first unit containing means for producing a time-varying magnetic field; and, a second unit containing means for detecting a magnetic field, the first and second units being sealed against entry of water at pressures of between about 80 PSIG and 120 PSIG, and the device being adapted such that the first unit and the second unit are maintained in a position during use to allow remote field eddy current inspection.

27. The inspection device as defined in claim 26 wherein the flexible connectors are formed of flexible tubing.

28. The inspection devise as defined in claim 26 wherein the series of housing units further comprises a unit sealed against entry of water and containing means for transmitting detected data along a transmitting line to a means for analyzing the data.

29. The inspection device as defined in claim 26 wherein the series of housing units further comprises a unit sealed against entry of water and containing means for storing detected data.

30. A remote field eddy current inspection device for water pipelines comprising a series of housing units having a shape suitable for passing through a water hydrant and a moving through a water pipeline system, a flexible connector extending between each of the housing units in series, at least one of the flexible connectors providing for communication between a pair of adjacent housing units and sealing means being disposed between the flexible connector and each of the pair of housing units to prevent passage of water into the housing units between which the flexible connector extends, and means for placing the device in tow, wherein the series of housing units comprises:

a first unit sealed against entry of water and containing means for producing a time-varying magnetic field; and, a second unit sealed against entry of water and containing means for detecting a magnetic field; and the device being adapted for use in water at pressures of between about 80 PSIG and 120 PSIG and further adapted such that the first unit and the second unit are maintained in a position during use to allow remote field eddy current inspection.

* * * * *